US 9,895,099 B2

(12) United States Patent
Rennaker

(10) Patent No.: US 9,895,099 B2
(45) Date of Patent: Feb. 20, 2018

(54) SYSTEM FOR ACCELERATION MEASUREMENTS AND TRAUMATIC BRAIN INJURY DETECTION

(71) Applicant: Board of Regents, The University of Texas System, Austin, TX (US)

(72) Inventor: Robert Rennaker, Sachse, TX (US)

(73) Assignee: Board of Regents, The University of Texas System, Austin, TX (US)

(*) Notice: Subject to any disclaimer, the term of this patent is extended or adjusted under 35 U.S.C. 154(b) by 62 days.

(21) Appl. No.: 14/633,996

(22) Filed: Feb. 27, 2015

(65) Prior Publication Data

US 2015/0245795 A1 Sep. 3, 2015

Related U.S. Application Data

(60) Provisional application No. 61/946,333, filed on Feb. 28, 2014.

(51) Int. Cl.
| | | |
|---|---|---|
| *A61B 5/00* | (2006.01) | |
| *A61B 5/11* | (2006.01) | |
| *G01P 15/03* | (2006.01) | |
| *G01P 15/135* | (2006.01) | |
| *A61B 5/01* | (2006.01) | |

(52) U.S. Cl.
CPC .......... *A61B 5/4064* (2013.01); *A61B 5/11* (2013.01); *A61B 5/6814* (2013.01); *G01P 15/036* (2013.01); *G01P 15/135* (2013.01); *A61B 5/0022* (2013.01); *A61B 5/01* (2013.01); *A61B 5/746* (2013.01); *A61B 2560/0475* (2013.01); *A61B 2562/0219* (2013.01)

(58) Field of Classification Search
CPC ....... A61B 5/4064; A61B 5/6814; A61B 5/11; G01P 15/001; G01P 15/00
USPC .......................................... 600/300
See application file for complete search history.

(56) References Cited

U.S. PATENT DOCUMENTS

| | | |
|---|---|---|
| 4,618,230 A | 10/1986 | Ens et al. |
| 5,422,690 A | 6/1995 | Rothberg et al. |
| 6,260,968 B1 | 7/2001 | Stark et al. |
| 7,988,287 B1 | 8/2011 | Butler et al. |
| 8,585,609 B2 | 11/2013 | Kiderman et al. |
| 2005/0096703 A1* | 5/2005 | Sanders ............ A61N 1/37252 607/14 |
| 2005/0099601 A1 | 5/2005 | MacDougall et al. |

(Continued)

FOREIGN PATENT DOCUMENTS

| | | |
|---|---|---|
| EP | 8585609 | 10/2013 |
| WO | WO 2013/023056 | 2/2013 |

OTHER PUBLICATIONS

Kumar, Shrawan, Robert Ferrari, and Yogesh Narayan. "Cervical Muscle Response to Whiplash-type Right Anterolateral Impacts." Eur Spine J 13.5 (2004): 398-407.*

(Continued)

*Primary Examiner* — Alyssa M Alter
(74) *Attorney, Agent, or Firm* — Labatt, LLC

(57) ABSTRACT

The present invention comprises apparatuses and methods of detecting impacts to the head. Accelerometers attached to a user's head and neck or body is used to measure the differential acceleration of the head with respect to the neck or body. A differential acceleration exceeding a certain threshold may be indicative of the user suffering a traumatic brain injury.

34 Claims, 2 Drawing Sheets

(56) References Cited

U.S. PATENT DOCUMENTS

| | | |
|---|---|---|
| 2009/0018419 A1 | 1/2009 | Torch |
| 2009/0213329 A1 | 8/2009 | Kandel et al. |
| 2011/0184320 A1 | 7/2011 | Shipps |
| 2012/0008091 A1 | 1/2012 | Stewart |
| 2013/0110415 A1* | 5/2013 | Davis .................... A42B 3/046 702/41 |
| 2013/0278899 A1 | 11/2013 | Waldorf |
| 2013/0308099 A1 | 11/2013 | Stack |
| 2014/0039355 A1 | 2/2014 | Crisco |
| 2014/0046193 A1 | 2/2014 | Stack |

OTHER PUBLICATIONS

International Search Report and Written Opinion issued in International Application No. PCT/US2015/018051, dated Jun. 2, 2015.

\* cited by examiner

SYSTEM FOR ACCELERATION MEASUREMENTS AND TRAUMATIC BRAIN INJURY DETECTION

CROSS-REFERENCE TO RELATED APPLICATIONS

This application claims priority to U.S. Provisional Patent Application Ser. No. 61/946,333, filed Feb. 28, 2014, the contents of which are incorporated by reference herein.

BACKGROUND OF THE INVENTION

1. Field of the Invention

The present invention relates generally to the field of detecting and measuring impacts to the head and resulting neurological impairment. More particularly, it concerns measuring the differential acceleration (including for example, a linear, angular, and/or rotational differential acceleration) of the head in comparison to the body to detect potential traumatic brain injury.

2. Description of Related Art

Traumatic brain injury is caused by head trauma after impact. The rapid acceleration or deceleration of the brain within the cranial vault, or absorption of a shock wave can cause the brain to impact the inside of the skull. These forces can also cause stretching and/or shearing of axonal tracts (tearing of connections between neuronal cells), which can trigger secondary neurodegenerative damage and maladaptive plasticity leading to chronic neurological dysfunction. The physiological effects resulting from these injuries can be detected immediately in some cases, but can also develop slowly over minutes, hours, weeks, months, or even years post-injury. Pathological processes can evolve slowly, making them difficult to detect in stages when interventions are most effective. Mild Traumatic Brain Injuries (mTBI) can result in post-concussion syndrome and impairment in cognitive domains such as memory, processing speed, affect, impulse control, prediction/planning and other executive functions as measured by traditional neuropsychological instruments. Acute physiological changes (e.g. inflammation) following mTBI may also make an individual more susceptible to a subsequent impact due to poor judgment or slower reaction times. These repeated impacts may, in turn, make an individual more susceptible to chronic neurological injury. Therapeutic options may be developed to prevent chronic neurological damage if we can identify reliable quantitative markers (changes in physiological and neurobehavioral responses) associated with mTBI. These quantitative measures could also be used in conjunction with acceleration measurements to identify those types of impacts associated with acute and chronic neurological injury. However, there are currently no devices capable of accurately and objectively tracking subtle changes in neurophysiological status associated with either mTBI or systems that accurately measure angular acceleration of the head correlated with mTBI biomarkers.

There is a critical need to identify a sensitive, rapid, easily obtainable biomarker to serve as an objective indicator of when an athlete or soldier should be withheld from the field and when they can return in order to avoid permanent traumatic brain injury. Repeated concussive and even subclinical exposures to head trauma can produce a spectrum of chronic traumatic encephalopathy (CTE), resulting in stress points of damage in the brain, ranging in severity from mild cognitive impairment to severe dementia, disinhibited violent outbursts, motor dysfunction, reduced quality of life and even suicide.

There are currently several wearable accelerometer units available commercially. While each provides an indication of linear acceleration/deceleration, none of the existing devices alone accurately measures differential acceleration of the head relative to the body, which may in fact be a key component in the production of concussion symptoms, as linear measures alone have shown limited correlations with concussion symptoms. It is likely that movement of the head relative to the body is a critical factor in traumatic brain injuries due to the tethering forces of the spine on the brain.

SUMMARY OF THE INVENTION

Exemplary embodiments of the present disclosure comprise an apparatus and method for measuring impacts to the head Exemplary embodiments, include an apparatus for measuring impacts to the head and body comprising: a processor; a first accelerometer electrically coupled to the processor and operably coupled to a head of a user; a second accelerometer electrically coupled to the processor and operably coupled to neck or body of a user; and a flexible frame coupled to the processor, the first accelerometer, and the second accelerometer. In specific embodiments, the processor is operable to calculate a difference in an acceleration of the first accelerometer and an acceleration of the second accelerometer to measure a differential acceleration of the head in comparison to the neck or body.

Certain embodiments include a third accelerometer electrically coupled to the processor, coupled to the flexible frame, and operably coupled behind an ear of a user, wherein the processor is operable to calculate a difference in an acceleration of the first accelerometer, an acceleration of the second accelerometer, and an acceleration of the third accelerometer to measure a rotational acceleration of the head in comparison to the neck.

Exemplary embodiments comprise a flexible frame incorporating a processor and multiple accelerometers. The first accelerometer can be situated on a user's head, and the second accelerometer can be situated on a user's neck or body. Upon an impact, the processor calculates the difference in acceleration between the first accelerometer and the second accelerometer to determine the degree of differential acceleration differential acceleration (including for example, a linear, angular, and/or rotational differential acceleration) of the user's head in comparison to the user's neck or body.

Some embodiments further comprise a third accelerometer situated behind or above the user's ear. Upon an impact, the processor calculates the difference in acceleration between the first, second, and third accelerometers to determine the degree of differential acceleration of the user's head in comparison to the user's neck. In some embodiments, each accelerometer detects acceleration in three axes. In some embodiments, the accelerometers are operable to detect accelerations of up to 200 G. In some embodiments, the accelerometers are removably attached to a user's skin using an adhesive. In some embodiments the sensors are worn in clothing (headbands, neckbands) or equipment (helmet, shoulder pads).

Some embodiments further comprise a light electrically coupled to the processor, which is illuminated when the processor measures differential acceleration (including for example, a linear, angular, and/or rotational differential acceleration) that exceeds a predetermined threshold. In some embodiments, the invention further comprises a speaker or vibrating buzzer electrically coupled to the processor, which emits a sound, warning tone and/or vibration when the processor measures a differential acceleration that exceeds a predetermined threshold.

Some embodiments further comprise a temperature sensor that is operable to measure a user's body temperature. In some embodiments, the invention further comprises a memory which is operable to record the measured accelerations that exceed a predetermined threshold. In some embodiments, the memory is operable to record the elapsed time between measured differential accelerations that exceed a predetermined threshold. In some embodiments, the memory is operable to record the user's body temperature at the time of an acceleration that exceeds a predetermined threshold.

Some embodiments further comprise metal contacts located in the frame and a separate base station. The base station is operable to be electrically coupled to the frame via the electrical contacts and to download the measured differential accelerations, the elapsed time, and the body temperatures from memory. In some embodiments, the invention further comprises a wireless transmitter in the frame. The wireless transmitter is operable to transmit the measured differential accelerations, the elapsed time, and the body temperatures from memory.

Some embodiments further comprise a switch electrically coupled to the processor, where the switch is operable to power on and power off the apparatus when a magnet is swiped over the switch a magnetic switch located in the frame. In particular embodiments, the switch is a magnetic switch. In some embodiments, the magnetic switch is operable to cause a light to flash green when a magnet is swiped over the magnetic switch and the memory has not recorded differential accelerations that exceed the predetermined threshold. In some embodiments, the magnetic switch is operable to cause a light to flash red when a magnet is swiped over the magnetic switch and the memory has recorded differential accelerations that exceed the predetermined threshold.

Certain embodiments comprise a method of measuring impacts to a user's head by attaching a first accelerometer to a user's head, attaching a second accelerometer to a user's neck or body, and measuring a differential acceleration of the head in comparison to the neck or body by comparing an acceleration of the first accelerometer to an acceleration of the second accelerometer.

Some embodiments further comprise attaching a third accelerometer above or behind the user's ear, and measuring the differential acceleration of the user's head in the comparison to the neck by comparing the linear, angular or differential of the third accelerometer to the second accelerometer. Some embodiments further comprise turning on a light when the invention measures a differential acceleration that exceeds a predetermined threshold. Some embodiments further comprise emitting a sound or warning tone when the invention measures a differential acceleration that exceeds a predetermined threshold. Some embodiments further comprise producing a vibration when the invention measures a differential acceleration that exceeds a predetermined threshold.

Some embodiments further comprise measuring a body temperature of the user using a temperature sensor. Some embodiments further comprise recording the differential acceleration, the elapsed time between differential accelerations, and the body temperature in a memory. Some embodiments further comprise transmitting the differential acceleration, the elapsed time between differential accelerations, and the body temperature to a base station via metal contacts. Certain embodiments further comprise wirelessly transmitting the differential acceleration, the elapsed time between differential accelerations, and the body temperature via a wireless transmitter.

Particular embodiments further comprise swiping a magnet over a magnetic switch to power on and power off components (e.g. a processor and accelerometers). Specific embodiments further comprise swiping a magnet over a magnetic switch to determine if the measured differential acceleration of the head exceeds the predetermined threshold and flashing a light green if the invention has not recorded a differential acceleration that has exceeded the predetermined threshold. In some embodiments, the invention further comprises swiping a magnet over a magnetic switch and flashing a light red if the invention has recorded a differential acceleration that has exceeded the predetermined threshold.

Exemplary embodiments include an apparatus for measuring impacts to the head comprising: a processor; a first accelerometer electrically coupled to the processor and operable to contact a head of a user; a second accelerometer electrically coupled to the processor and operable to contact a neck or body of a user; and a flexible frame coupled to the processor, the first accelerometer, and the second accelerometer; where the processor is operable to calculate a difference in an acceleration of the first accelerometer and an acceleration of the second accelerometer to measure a differential acceleration of the head in comparison to the neck or body.

Certain embodiments further comprise a third accelerometer electrically coupled to the processor, coupled to the flexible frame, and operable to contact behind an ear of a user, where the processor is operable to calculate a difference in an acceleration of the first accelerometer, an acceleration of the second accelerometer, and an acceleration of the third accelerometer to measure a differential acceleration of the head in comparison to the neck. In particular embodiments, the accelerometers detect acceleration in three axes. In specific embodiments, the accelerometers are removably attached to a user's skin using an adhesive or in clothing or equipment.

Certain embodiments comprise a light electrically coupled to the processor, wherein the processor is operable to turn on the light when the measured differential acceleration of the head exceeds a predetermined threshold. In certain embodiments the light may be wirelessly coupled to the processor. Particular embodiments further comprise a speaker electrically coupled to the processor, where the processor is operable to emit a sound through the speaker when the measured differential acceleration of the head exceeds a predetermined threshold. Specific embodiments further comprise a vibrating buzzer electrically coupled to the processor, wherein the processor is operable to turn on the buzzer when the measured differential acceleration of the head exceeds a predetermined threshold. In particular embodiments, the accelerometers are operable to measure an acceleration up to 200 G. Specific embodiments further comprise a memory electrically coupled to the processor, where the memory is operable to record the measured differential accelerations that exceed a predetermined threshold. In certain embodiments, the memory is operable to record an elapsed time between the measured differential accelerations that exceed a predetermined threshold.

Particular embodiments further comprise a temperature sensor electrically coupled to the processor and operable to contact skin of the user, wherein the memory is operable to record a body temperature of a user. Some embodiments further comprise metal contacts electrically coupled to the processor; and a base station, wherein the base station is operable to be electrically coupled to the metal contacts and to download measured differential accelerations from the memory. Particular embodiments further comprise metal contacts electrically coupled to the processor; and a base station, where the base station is operable to be electrically coupled to the metal contacts and to download measured differential accelerations and the elapsed time from the memory.

Specific embodiments further comprise metal contacts electrically coupled to the processor; and a base station, where the base station is operable to be electrically coupled to the metal contacts and to download the measured differential accelerations, the elapsed time, and the body temperatures from the memory. Particular embodiments further comprise a wireless transmitter electrically coupled to the processor, where the wireless transmitter is operable to transmit the measured differential accelerations, the elapsed time, or the body temperature. Some embodiments further comprise a switch (including for example, a magnetic or mechanical switch) electrically coupled to the processor, where the switch is operable to power on and power off the apparatus when a magnet is swiped over the switch. In specific embodiments, the light is operable to flash a red light when a magnet is swiped over a magnetic switch if the memory recorded measured differential accelerations that exceeded a predetermined threshold and is operable to flash a green light when a magnet is swiped over the magnetic switch if the memory did not record differential accelerations that exceeded a predetermined threshold.

Exemplary embodiments include a method of measuring impacts to the head comprising: attaching a first accelerometer to a head of a user; attaching a second accelerometer to a neck or body of a user; and measuring a differential acceleration of the head in comparison to the neck or body by comparing an acceleration of the first accelerometer to an acceleration of the second accelerometer.

Certain embodiments include a method of measuring impacts to the head further comprising attaching a third accelerometer behind an ear or another location on the head of a user and measuring a differential acceleration of the head in comparison to the neck by comparing an acceleration of the third accelerometer to an acceleration of the second accelerometer. In particular embodiments, a light turns on when the measured differential acceleration of the head exceeds a predetermined threshold. In specific embodiments, a warning tone is emitted when the measured differential acceleration of the head exceeds a predetermined threshold. In certain embodiments, a vibration is produced when the measured differential acceleration of the head exceeds a predetermined threshold. In exemplary embodiments, a body temperature of the user is measured using a temperature sensor. Particular embodiments further comprise recording the differential acceleration in a memory. Specific embodiments further comprise recording an elapsed time between the recorded differential accelerations in a memory. Some embodiments further comprise recording the body temperature in a memory. Certain embodiments further comprise transmitting the recorded differential acceleration to a holder via metal contacts. Particular embodiments further comprise transmitting the elapsed time to a holder via metal contacts. Some embodiments further comprise transmitting the recorded body temperature to a holder via metal contacts. Specific embodiments further comprise transmitting the recorded differential acceleration via a wireless transmitter. Exemplary embodiments further comprising transmitting the elapsed time via a wireless transmitter.

Certain embodiments further comprise wirelessly transmitting the recorded body temperature via a wireless transmitter. Particular embodiments further comprise swiping a magnet over a magnetic switch to power on and off a processor and accelerometers. Specific embodiments further comprise swiping a magnet over a magnetic switch to determine if the measured differential acceleration of the head exceeds the predetermined threshold.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein the term "differential acceleration" includes a linear, angular, and/or rotational differential acceleration.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. Embodiments of the invention may be better understood by reference to one or more of these drawings in combination with the detailed description of specific embodiments presented herein.

DESCRIPTION OF ILLUSTRATIVE EMBODIMENTS

Exemplary embodiments of the present disclosure are designed to detect physiological changes associated with mild traumatic brain injuries and quantify accelerations associated with mTBI. One exemplary embodiment (also referred to herein as the "Second Derivative System") monitors and integrates directional and differential acceleration data from an unobtrusive, player-worn sensor. Embodiments of the invention may include web based applications that will allow the data to be collected and analyzed in real time. The Second Derivative System may predict the long-term neurological consequences of mTBI. The device may prove useful in providing the information needed to develop strategies, rules, and interventions to minimize neurological damage due to head impacts.

Figure 1:
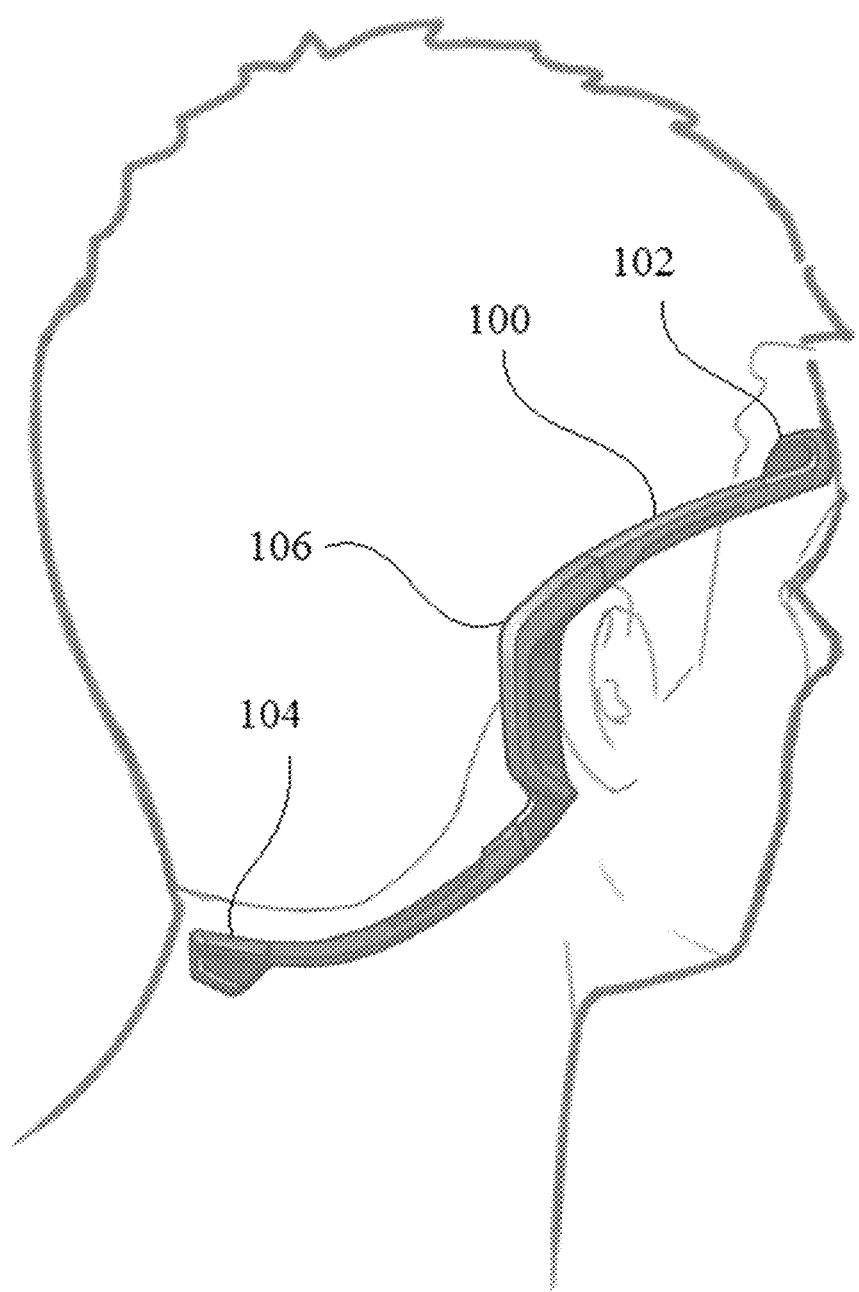
FIG. 1—An exemplary embodiment of the present disclosure installed on a user's head.
Figure 2:
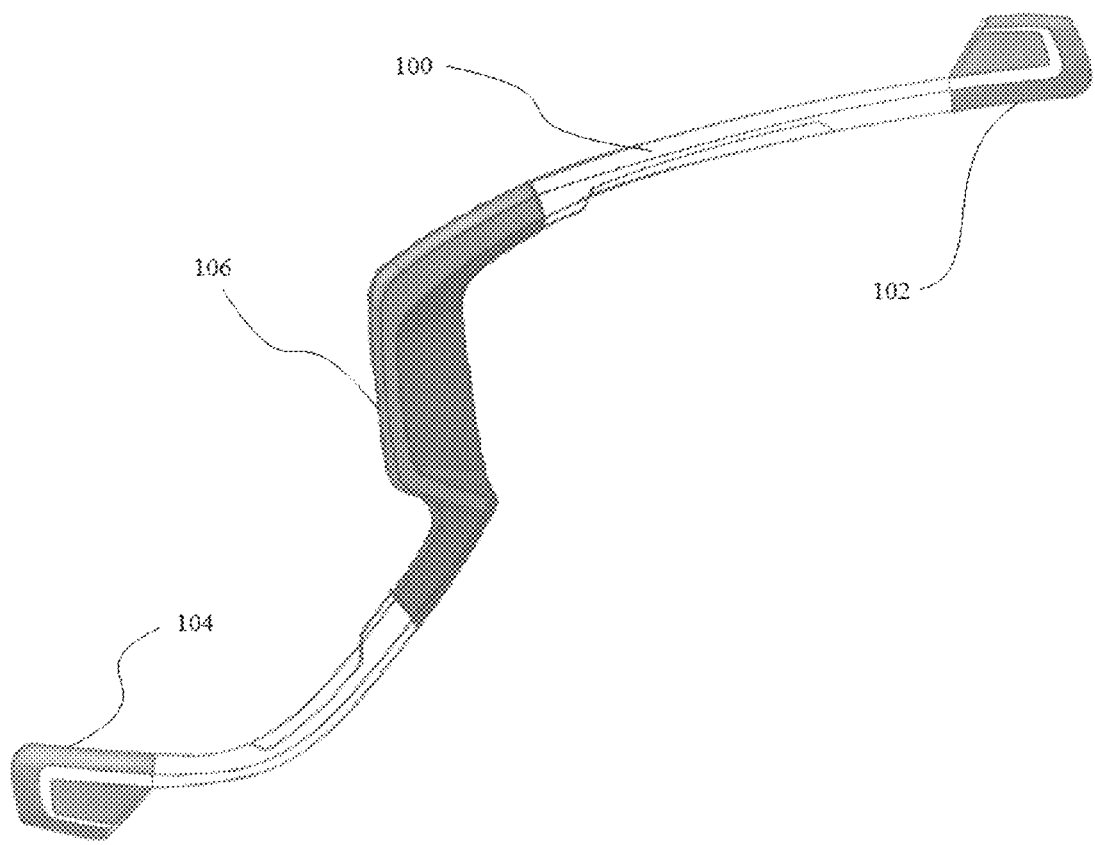
FIG. 2—The exemplary embodiment of FIG. 1 in isolation.

Second Derivative Sensor:

Exemplary embodiments of the device include a series of two or three accelerometers unobtrusively positioned on the head and neck to accurately measure and record linear and angular rotation. In certain embodiments, the accelerometers are mounted in a flexible or compliant frame forming a lightweight device, positioned at the ends and middle of the device with a separation of one to two inches between sensors. This configuration permits measurement of head rotation in all three axes relative to the body/neck. It is believed that it is the relative motion between various brain structures and the spine that results in neural injury following impacts. Impacts that result in angular accelerations of the head are most likely to cause tearing of axons and blood vessels due to the tensile forces generated. The compliant frame conforms to the head, running from the temple, behind the ear and down around the neck (as shown in FIG. 1). It is attached to the skin using non-irritating adhesive at the ends of the arms and at the center behind the ear. The arms are thin and detachable, and can be bent in multiple configurations to custom fit the individual.

Second Derivative System Design.

In exemplary embodiments, the Second Derivative System uses a low-power TI MSP430 processor, 200G 3 axis accelerometers from Analog Devices, with signal conditioning circuitry, 2 MB of FRAM for low-power memory storage, and a small, rechargeable Lithium Ion battery. The MSP430 processor has a real-time clock and USB control for programming and battery recharging.

FIG. 1 depicts the Second Derivative System worn on a user's head. A first accelerometer 102 is located on the user's forehead or temple above the right eye. A second accelerometer 104 is located on the back of the user's neck. A third accelerometer 106 is located above or behind the user's right ear. A "S" shaped, flexible or compliant frame 100 is coupled to the first accelerometer 102, second accelerometer 104, and third accelerometer 106. In preferred embodiments, the frame 100 is made of plastic and/or rubber. Disposed within the frame 100 is a processor that is electrically coupled to the first accelerometer 102, second accelerometer 104, and third accelerometer 106. The processor receives signals from each accelerometer indicating the magnitude and direction of acceleration. To determine the differential acceleration of the head in comparison to the neck, the processor calculates the difference in acceleration of the first and third accelerometers when compared to the second accelerometer. A calculated differential acceleration that exceeds a certain predetermined threshold may be indicative of the wearer sustaining a mild traumatic brain injury.

In some embodiments, if the calculated differential acceleration exceeds a predetermined threshold, the processor may cause a light emitting diode (LED) to blink red. In other embodiments, if the calculated differential acceleration exceeds a predetermined threshold, the processor may cause a speaker near the wearer's ear to emit a warning tone. In other embodiments, if the calculated differential acceleration exceeds a predetermined threshold, the processor may cause a buzzer to vibrate against the wearer's skin.

In preferred embodiments, the Second Derivative System includes memory for storing differential acceleration data. In some embodiments, the memory stores the magnitude of the greatest calculated differential acceleration and time stamp. In other embodiments, the memory stores the magnitude of each calculated differential acceleration that exceeds the predetermined threshold. In some embodiments, the memory further stores the elapsed time between events that exceed the predetermined acceleration threshold.

The Second Derivative System may include a temperature sensor for measuring the body temperature of the wearer. It is theorized that higher body temperature and increased blood pressure during strenuous activity will cause increased cranial pressure and make an individual more susceptible to head injuries. The processor may use the wearer's body temperature, along with the calculated differential acceleration data, to predict the occurrence of a mild traumatic brain injury. In some embodiments, the memory further stores the wearer's body temperature at the time of the event that exceeded the predetermined acceleration threshold.

A magnetic switch (magnetically actuated) on the device may be used to turn the sensor on and off as well as to allow an athletic trainer to check the subject for symptoms related to registered impacts. In some embodiments, swiping a magnet over the device for 4 seconds turns the device on and off. In some embodiments, swiping a magnet over the device for less than 1 second will cause the sensor to report if an impact or rotation threshold was exceeded. An LED may blink red if a predetermined impact threshold was exceeded or blink green if impact thresholds were not exceeded. In other embodiments, a small speaker will emit a warning tone in the user's ear if a predetermined impact threshold was exceeded. In other embodiments, a vibrating buzzer will alert the user if a predetermined impact threshold was exceeded. The device can be programmed with multiple impact thresholds based on linear and/or angular acceleration measures.

In some embodiments, the Second Derivative System is paired with a base station. The Second Derivative System and the base station both have metal electrical contacts. When the Second Derivative System is placed in the base station, the device's battery is recharged through the electrical contacts. In some embodiments, the base station downloads data from the device's memory through the electrical contacts. The base station may also upload firmware updates to the device through the electrical contacts. The electrical contacts may consist of a mini USB connector, micro USB connector, FireWire connector, or a proprietary connector. The base station may be a tablet, laptop computer, smartphone, or other computing device.

The Second Derivative System may include a wireless transmitter to transmit accelerometer and/or temperature sensor data. The data may be transmitted to a holder, tablet, laptop computer, smartphone, or other computing device. In preferred embodiments, the data is encrypted prior to transmission. The wireless transmission may use the 802.11, Bluetooth, or IrDA protocols.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An apparatus for measuring impacts to the head and body comprising:
   a processor;
   a first accelerometer electrically coupled to the processor and configured for coupling to a head of a user;
   a second accelerometer electrically coupled to the processor and configured for coupling to a neck or body of a user; and
   a flexible frame coupled to the processor, the first accelerometer, and the second accelerometer;
   wherein the processor is configured to calculate a difference in an acceleration of the first accelerometer and an acceleration of the second accelerometer to measure a differential acceleration of the head in comparison to the neck or body.

2. The apparatus of claim 1, further comprising a third accelerometer electrically coupled to the processor, coupled to the flexible frame, and configured for coupling behind an ear of a user, wherein the processor is configured to calculate a difference in an acceleration of the first accelerometer, an acceleration of the second accelerometer, and an acceleration of the third accelerometer to measure a rotational acceleration of the head in comparison to the neck.

3. The apparatus of claim 1, wherein the first and second accelerometers detect acceleration in three axes.

4. The apparatus of claim 1, wherein the first and second accelerometers are removably attached to a user's skin using an adhesive or mounted to clothing or equipment coupled to the user.

5. The apparatus of claim 1 further comprising a light electrically coupled to the processor, wherein the processor is configured to turn on the light when the measured differential acceleration of the head exceeds a predetermined threshold.

6. The apparatus of claim 1 further comprising a speaker electrically coupled to the processor, wherein the processor is configured to emit a sound through the speaker when the measured differential acceleration of the head exceeds a predetermined threshold.

7. The apparatus of claim 1 further comprising a vibrating buzzer electrically coupled to the processor, wherein the processor is configured to turn on the buzzer when the measured differential acceleration of the head exceeds a predetermined threshold.

8. The apparatus of claim 1, wherein the first and second accelerometers are configured to measure an acceleration up to 200 G.

9. The apparatus of claim 1, further comprising a memory electrically coupled to the processor, wherein the memory is configured to record the measured differential accelerations that exceed a predetermined threshold.

10. The apparatus of claim 9, wherein the memory is configured to record an elapsed time between the measured differential accelerations that exceed a predetermined threshold.

11. The apparatus of claim 10, further comprising metal contacts electrically coupled to the processor; and a base station, wherein the base station is configured to be electrically coupled to the metal contacts and to download measured differential accelerations and the elapsed time from the memory.

12. The apparatus of claim 9, further comprising metal contacts electrically coupled to the processor; and a base station, wherein the base station is configured to be electrically coupled to the metal contacts and to download measured differential accelerations from the memory.

13. The apparatus of claim 9, further comprising a temperature sensor electrically coupled to the processor and configured to contact skin of the user, wherein the memory is configured to record a body temperature of a user or a surrounding temperature.

14. The apparatus of claim 13, further comprising metal contacts electrically coupled to the processor; and a base station, wherein the base station is configured to be electrically coupled to the metal contacts and to download the measured differential acceleration, and the body temperature from the memory.

15. The apparatus of claim 1, further comprising a wireless transmitter electrically coupled to the processor, wherein the wireless transmitter is configured to transmit the measured differential acceleration.

16. The apparatus of claim 1, further comprising a switch electrically coupled to the processor, wherein the switch is configured to power on and power off the apparatus when a magnet is swiped over the switch.

17. The apparatus of claim 16, wherein the switch is a magnetic switch and wherein a light is configured to flash a red light when a magnet is swiped over the magnetic switch if the memory recorded measured differential accelerations that exceeded a predetermined threshold and wherein the light is configured to flash a green light when a magnet is swiped over the magnetic switch if the memory did not measure differential accelerations that exceeded a predetermined threshold.

18. A method of measuring impacts to the head comprising:
   attaching a first accelerometer to a head of a user;
   attaching a second accelerometer to a neck or body of a user; and
   measuring a differential acceleration of the head in comparison to the neck or body by comparing an acceleration of the first accelerometer to an acceleration of the second accelerometer.

19. The method of claim 18, further comprising attaching a third accelerometer behind an ear of a user and measuring a rotational acceleration of the head in comparison to the neck by comparing an acceleration of the third accelerometer to an acceleration of the second accelerometer.

20. The method of claim 18, wherein a light turns on when the measured differential acceleration of the head exceeds a predetermined threshold.

21. The method of claim 18, wherein a warning tone is emitted when the measured differential acceleration of the head exceeds a predetermined threshold.

22. The method of claim 18, wherein a vibration is produced when the measured differential acceleration of the head exceeds a predetermined threshold.

23. The method of claim 18, wherein a body temperature of the user is measured using a temperature sensor.

24. The method of claim 23, further comprising recording the body temperature in a memory.

25. The method of claim 24, further comprising wirelessly transmitting the recorded body temperature via a wireless transmitter.

26. The method of claim 24, further comprising transmitting the recorded body temperature to a holder via metal contacts.

27. The method of claim 18, further comprising swiping a magnet over a magnetic switch to power on and off a processor and accelerometers.

28. The method of claim 27, further comprising swiping a magnet over a magnetic switch to determine if the measured differential acceleration of the head exceeds the predetermined threshold.

29. The method of claim 18, further comprising recording the differential acceleration in a memory.

30. The method of claim 29, further comprising transmitting the recorded differential acceleration via a wireless transmitter.

31. The method of claim 29 further comprising transmitting the recorded differential acceleration to a holder via metal contacts.

32. The method of claim 29, further comprising recording an elapsed time between the recorded differential accelerations in a memory.

33. The method of claim 32, further comprising transmitting the elapsed time to a holder via metal contacts.

34. The method of claim 32, further comprising transmitting the elapsed time via a wireless transmitter.

* * * * *